United States Patent [19]

Mitchell

[11] 4,169,183
[45] Sep. 25, 1979

[54] 9-DIALKYLAMINO-SPIRO [6H-[1]BENZOPYRANO[3,2-G]QUINOLINE-6,1'(3'H)-ISOBENZOFURAN]-3'-ONE COMPOUNDS AND PRESSURE-SENSITIVE RECORDING SYSTEM THEREWITH

[75] Inventor: Nancy G. Mitchell, Grand Island, N.Y.

[73] Assignee: Moore Business Forms, Inc., Grand Island, N.Y.

[21] Appl. No.: 902,730

[22] Filed: May 3, 1978

Related U.S. Application Data

[63] Continuation-in-part of Ser. No. 774,015, Mar. 3, 1977, abandoned.

[51] Int. Cl.² ............................................. B32B 3/26
[52] U.S. Cl. .................................. 428/307; 260/335; 252/316; 282/27.5; 427/151; 542/401; 546/15
[58] Field of Search .................. 542/401; 260/295 A, 260/335; 428/307, 306; 282/27.5; 252/316; 427/151

[56] References Cited

U.S. PATENT DOCUMENTS 3,988,492  10/1976  Spatz ................................... 282/27.5
3,996,406  12/1976  Alsop ................................... 427/151

*Primary Examiner*—Arthur P. Demers
*Attorney, Agent, or Firm*—Watson, Cole, Grindle & Watson

[57] ABSTRACT

Disclosed are normally substantially colorless chromogenic 9-dialkylamino-spiro[6H-[1]benzopyrano[3,2-g]quinoline-6,1'(3'H)-isobenzofuran]-3'-one color precursor compounds having the following structural formula:

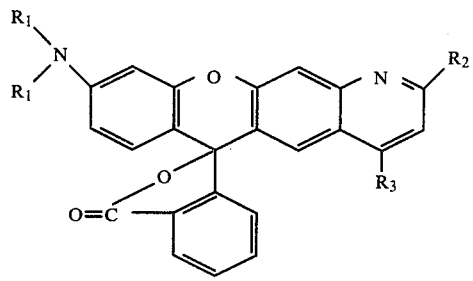

wherein each $R_1$ represents a lower alkyl group having from one to five carbon atoms and wherein each of $R_2$ and $R_3$ represents either a methyl group or a group which includes a methylene bridge resonance path having up to four carbon atoms, but wherein when $R_3$ is a methylene bridge resonance path-containing group, $R_2$ is not a methyl group. These compounds are initially substantially colorless but are capable of becoming highly colored when brought into reactive contact with many Lewis acid materials and the like. Accordingly, these compounds are highly useful as a component of pressure-sensitive copying papers.

25 Claims, No Drawings

9-DIALKYLAMINO-SPIRO [6H-[1]BENZOPYRANO[3,2-G]QUINOLINE-6,1'(3'H)-ISOBENZOFURAN]-3'-ONE COMPOUNDS AND PRESSURE-SENSITIVE RECORDING SYSTEM THEREWITH

This application is a continuation-in-part application of my prior application Ser. No. 774,015 filed on Mar. 3, 1977, now abandoned.

BACKGROUND OF THE INVENTION

1. Field of the Invention

The present invention relates to initially colorless, color precursor compounds having particular utility in the field of carbonless copying. The compounds may be utilized, for example, in the production of self-marking impact papers of the transfer or manifold type wherein a first marking ingredient is carried on one sheet of paper for reaction with a second marking ingredient normally carried on a mating sheet of paper. Specifically, the invention relates to a family of chromogenic 9-dialkylaminospiro[6H-[1]benzopyrano[3,2-g]quinoline-6,1'(3'H)-isobenzofuran]-3'-one color precursor compounds having the following structural formula:

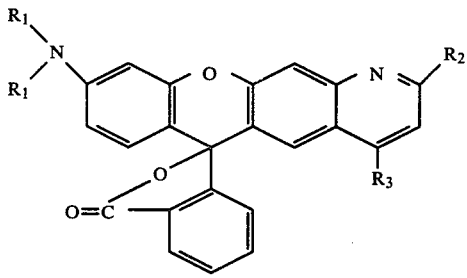

wherein each $R_1$ represents a lower alkyl group having from one to five carbon atoms and wherein each of $R_2$ and $R_3$ represents either a methyl group or a group which includes a methylene bridge resonance path having up to four carbon atoms, but wherein when $R_3$ is a methylene bridge resonance path-containing group, $R_2$ is not a methyl group. The term methylene bridge resonance path having up to four carbon atoms signifies a substituted alkenyl group of 2 to 4 carbon atoms in which the substituents are selected from phenyl or naphthyl, unsubstituted or substituted by nitro or amino groups, or from a heterocyclic radical.

2. Description of the Prior Art

Impact or pressure-sensitive carbonless transfer papers have recently come into wide usage in the United States and throughout the world. Ordinarily, such papers are printed and collated into manifolded sets capable of producing multiple copies. In this connection, pressure applied to the top sheet causes a corresponding mark on each of the other sheets of the set.

The top sheet of paper, upon which the impact or pressure is immediately applied, ordinarily has its back surface coated with microscopic capsules containing one of the reactive ingredients which produce a mark. A receiver sheet, placed in contact with such back face of the top sheet has its front surface coated with a material having a component reactive with the contents of the capsules so that when capsules are ruptured upon impact by stylus or machine key, the initially colorless or substantially colorless contents of the ruptured capsules react with a coreactant therefor on the receiver sheet and a mark forms on the receiver sheet corresponding to the mark impressed by the stylus or machine key.

In the art, impact transfer papers are designated by the terms CB, CFB and CF, which stand respectively for "coated back," "coated front and back" and "coated front." Thus, the CB sheet is usually the top sheet and the one on which the impact impression is directly made; the CFB sheets are the intermediate sheets, each of which has a mark formed on the front surface thereof and each of which also transmits the contents of ruptured capsules from its back surface to the front of the next succeeding sheet; and the CF sheet is the last sheet and is only coated on its front surface to have an image formed thereon. The CF sheet is not normally coated on its back surface as no further transfer is desired.

While it is customary to coat the capsules on the back surface and to coat the co-reactant for the capsules' contents on the front surface of each sheet, this procedure could be reversed if desired. Further, with some systems, coatings need not be used at all and the co-reactive ingredients may be carried in the sheets themselves, or one may be carried in one of the sheets and the other may be carried as a surface coating. Further, the reactants may both comprise microencapsulated liquids. Patents illustrative of many of the various kinds of systems which may incorporate such coreactive ingredients and which may be used in the production of manifolded transfer papers include, for example, U.S. Pat. No. 2,229,694 to Green, U.S. Pat. No. 2,712,507 to Green U.S. Pat. No. 3,016,308 to Macaulay, U.S. Pat. No. 3,429,827 to Ruus and U.S. Pat. No. 3,720,534 to Macaulay et al.

The most common variety of carbonless impact transfer paper, and the type with which the compounds of the present invention are preferably utilized, is the type illustrated, for example, in Green (U.S. Pat. No. 2,712,507) and Macaulay (U.S. Pat. No. 3,016,308) wherein microscopic capsules containing a liquid fill comprising a solution of an initially colorless chemically reactive color forming dye precursor are coated on the back surface of the sheet, and a dry coating of a coreactant chemical for the dye precursor is coated on the front surface of a receiving sheet.

Many color precursors useful in connection with carbonless copying systems are known to those skilled in the art to which the present invention pertains. For example, specific reference is made to the color precursors mentioned in the patent to Phillips, Jr. et al., U.S. Pat. No. 3,455,721 and particularly to those listed in the paragraph bridging columns 5 and 6 thereof. A variety of fluoran type color precursors are also disclosed in U.S. Pat. Nos. 3,501,331, 3,617,335, 3,669,711, 3,669,712 and 3,697,540 to Kimura et al., in U.S. Pat. Nos. 3,627,787 and 3,681,390 in Lin and in U.S. Pat. No. 3,725,416 to Yamamoto et al. These materials are capable of reacting with a CF coating containing an acidic material such as the acid-leached bentonite-type clay disclosed in U.S. Pat. No. 3,963,852 to Baxter issued June 15, 1976 (the entirety of which is hereby specifically incorporated by reference) or the acid-reactant organic polymeric material disclosed in the Phillips, Jr. et al. U.S. Pat. No. 3,455,721.

Many of the color precursors disclosed in the patents referred to above are capable of undergoing an acid-base type reaction with an acidic material. Other previously known color precursors are the spiro-dipyran compounds disclosed in the patent to Harbort, U.S. Pat. No. 3,293,060 with specific reference being made to the disclosure of the U.S. Pat. No. 3,293,060 patent extending from column 11, line 32 through column 12, line 21; the compounds disclosed in the patents to Alsop, U.S. Pat. Nos. 3,930,108, 3,928,685 and 3,929,828; and the fluoran compounds disclosed in the patent to Hoover, U.S. Pat. No. 3,787,325. The color precursors disclosed in the foregoing patents are generally initially colorless and are capable of becoming highly colored when brought into contact with acidic layer such as an acid-leached bentonite-type clay or an acid-reacting polymeric material, or the like. A continuing search, however, is being conducted by those familiar with the carbonless copy system filed to discover additional color precurser compounds which will be reasonably inexpensive and easily available which will produce a wide range of vivid colors, and which will be sufficiently stable for long-term storage.

Generally speaking, the color precursor materials now known to the art are dissolved in a solvent and the resulting solution is encapsulated in accordance with the procedures and processes described and disclosed by Macaulay (U.S. Pat. No. 3,016,308) and by Green U.S. Pat. No. 2,712,507) as mentioned above. Other processes for encapsulating color precursors are disclosed in U.S. Pat. No. 3,429,827 to Ruus and U.S. Pat. No. 3,578,605 to Baxter. In this connection, it should be mentioned that the exact nature of the capsule itself is not critical as long as the same is capable of containing the color precursor and can be ruptured by the application of pressure in accordance with conventional carbonless copying procedures. Solvents known to be useful in connection with dissolving color precursors include chlorinated biphenyls, vegetable oils (castor oil, coconut oil, cotton seed oil, etc.), esters (dibutyl adipate, dibutyl phthalate, butyl benzyl adipate, benzyl octyl adipate, tricresyl phosphate, trioctyl phosphate, etc.), petroleum derivatives (petroleum spirits, kerosene, mineral oils, etc.), aromatic solvents (benzene, toluene, etc.) silicone oils, or combinations of the foregoing. Particularly useful are the alkylated naphthalene solvents disclosed in U.S. Pat. No. 3,806,463 to Konishi et al.

For a disclosure of acidic coatings which are capable of converting the color precursors into their highly colored form, reference is made to the disclosures of U.S. Pat. Nos. 3,622,364, 3,330,722, 3,389,007 and 3,293,060, as well as to the disclosure of U.S. Pat. No. 3,963,852 to Baxter referred to above.

In the color forming systems outlined above, as will be appreciated by those skilled in the art, the color precursors are conventionally contained in pressure rupturable microcapsules which are included in the back coatings of the sheets of carbonless copying manifolded sets. Further, it will be appreciated that the acidic coatings are generally utilized as front coatings with the color precursor material in a solvent therefor being transferred from an adjacent back coating to the acidic layer front coating upon rupture of the capsules which contain the color precursor material.

SUMMARY OF THE INVENTION

It is an object of this invention to provide new and improved compounds having chromogenic properties and which may be incorporated in a paper sheet or coated onto the surface thereof to provide a manifolding unit, and which are, moreover, useful in carrying out improved methods of marking involving reactive contact with a color-activating material to yield vividly colored reaction products in areas where marking is desired.

It is another object of this invention to provide chromogenic compounds which are substantially colorless or only slightly colored offering a new and improved variety of chromogenic characteristics and yielding novel vividly colored substances upon contact with color-activating materials.

It is a further object of this invention to provide new and improved, normally substantially colorless, chromogenic substances which are stable and which yield stable colored reaction products when placed in reactive contact with Lewis acid materials or the like.

The foregoing objects are achieved by the provision of a family of substantially colorless chromogenic 9-dialkylamino-spiro [6H-[1]benzopyrano[3,2-g]quinoline-6,1'(3'H)-isobenzofuran]-3'one color precursor compounds having the following structural formula:

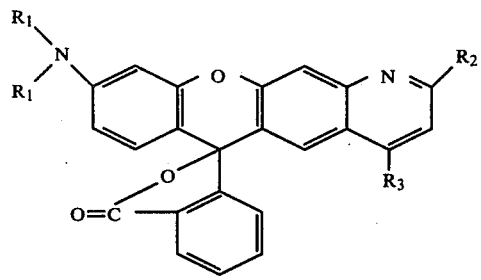

wherein each $R_1$ represents a lower alkyl group having from one to five carbon atoms and wherein each of $R_2$ and $R_3$ represents either a methyl group or a group which includes a methylene bridge resonance path having up to four carbon atoms, but wherein when $R_3$ is a methylene bridge resonance path-containing group $R_2$ is not a methyl group. The term methylene bridge resonance path having up to four carbon atoms signifies a substituted alkenyl group of 2 to 4 carbon atoms in which the substituents are selected from phenyl or naphthyl, unsubstituted or substituted by nitro or amino groups, or from a heterocyclic radical.

It should be noted that the fluoran compounds according to the present invention, and especially the 9-(diethylamino)-2,4-dimethylspiro [6H-[1] benzopyrano [3,2 g] quinoline-6,1'(3'H)-isobenzofuran]-3'-one compound, are distinct from the fluoran compounds taught in Hoover, U.S. Pat. No. 3,787,325 mentioned above. This is true not only because of the basic structure thereof, but also due to the distinctness in resonance between the structures. For example, the resonating structures of 9-(diethylamino)-2,4-diethylspiro [6H-[1] benzopyrano [3,2 g] quinoline-6,1' (3'H)-isobenzofuran]-3'-one coibute to color formation on contact with CF as follows:

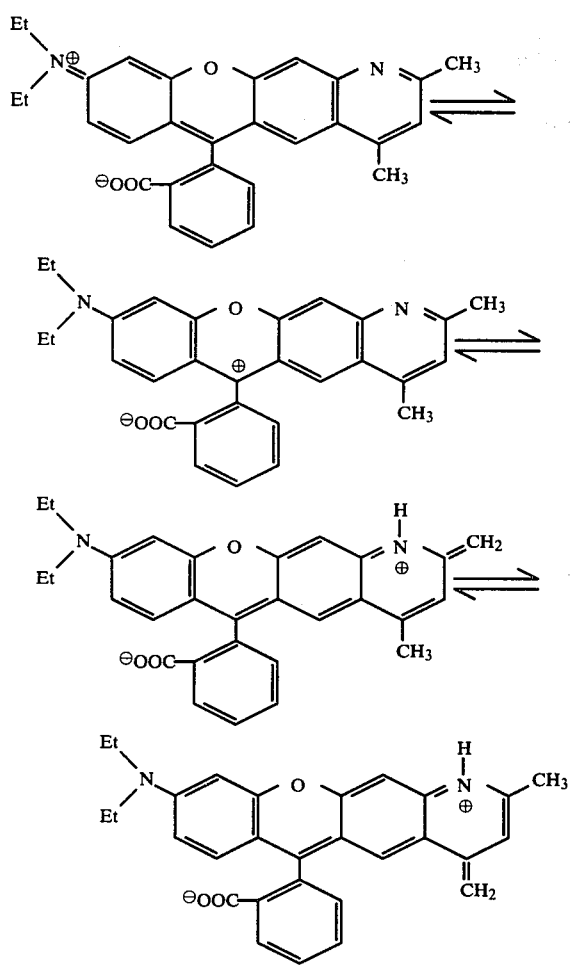

The compound described in Hoover, i.e., when the formula at column 1, line 47–55 an $R^1$ of ethyl; $R^2$ of methyl; $n=2$; and the methyl groups are appropriately placed, the following structure is obtained:

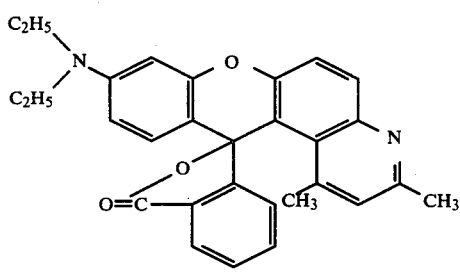

However, this compound resonates as follows:

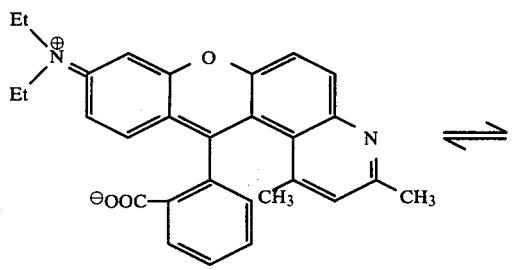

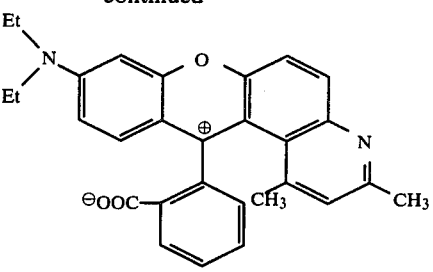

-continued

It is believed that these tautomeric forms of Hoover do not contribute to color formation, whereas the resonating structure of the present fluoran compounds do indeed contribute to color formation. In addition, the colors formed by the dye precursors of Hoover are less stable than the colors produced by the dye precursors according to the present invention.

DETAILED DESCRIPTION OF THE PREFERRED EMBODIMENTS

As noted above, broadly speaking the present invention is directed to a family of normally substantially colorless chromogenic 9-dialkylamino-spiro[6H-[1]benzopyrano[3,2-g]quinoline-6,1'  (3'H)-isobenzofuran]-3'-one color precursor compounds as identified structurally above and wherein $R_1$ represents a lower alkyl group having from one to five carbon atoms and wherein each of $R_2$ and $R_3$ represents either a methyl group or a group which includes a methylene bridge resonance path having up to four carbon atoms therein. However, when $R_3$ is a group which contains a methylene bridge resonance path, $R_2$ cannot be a methyl group. Thus, according to the present invention $R_1$ can be methyl, ethyl, propyl, butyl or pentyl; and $R_2$ and $R_3$ can be selected from methyl, or a group containing —CH=CH—, —CH=CH—CH=, or —CH=CH—CH=CH—. Preferably, each $R_1$ represents an ethyl group and each of $R_2$ and $R_3$ represents a methyl group.

These fluoran compounds are substantially colorless; however, when brought into contact with a solid Lewis acid electron-acceptor material such as the acid-leached bentonite-type clay disclosed in U.S. Pat. No. 3,963,852 to Baxter, they may be converted into a highly colored form. Various other solid acidic materials which are generally capable of converting these compounds into their highly colored form are disclosed in U.S. Pat. Nos. 3,622,364, 3,330,722, 3,389,007 and 3,293,060 referred to above.

The fluoran compounds of the present invention, which may also be generically identified as 9-dialkylamino-2,4-disubstituted-spiro [6H-[1] benzopyrano [3,2-g] quinoline-6,1'(3'H)isobenzofuran]-3'-one compounds, may be prepared by reacting one mole of an appropriate 4'-dialkylamino-2'-hydroxybenzoyl benzoic acid with one mole of an appropriate 7-hydroxy-2,4-disubstituted quinoline in the presence of a condensing agent such as sulfuric acid. The reaction scheme is as follows:

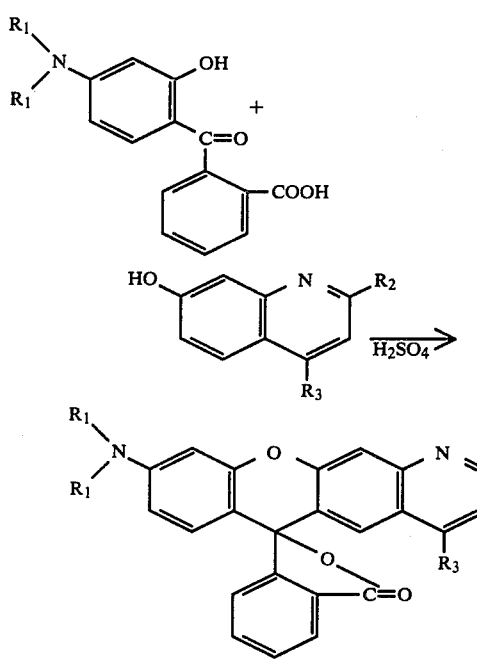

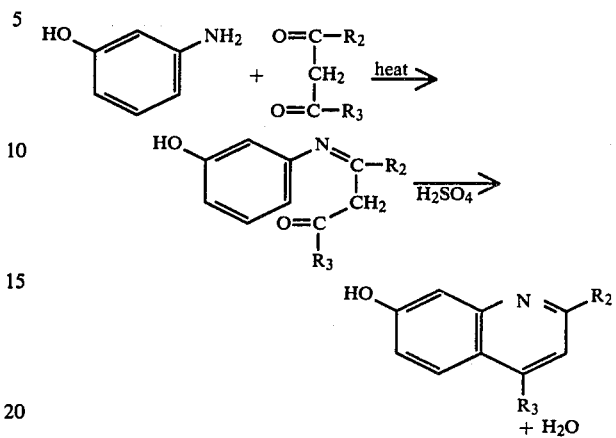

wherein $R_2$ and $R_3$ are as defined above.

The preferred fluoran compound according to the present invention is formed as follows:

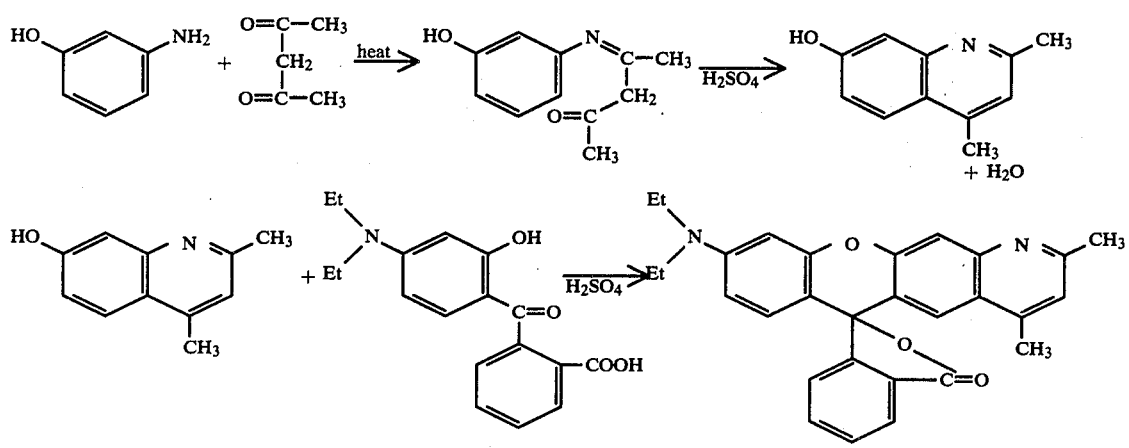

wherein $R_1$, $R_2$ and $R_3$ are as defined above.

The 7-hydroxy-2,4-disubstituted quinoline may itself be produced by reacting one mole of m-aminophenol with one mole of diketone in the presence of a condensing agent such as sulfuric acid. The reaction scheme is as follows:

However, various other fluoran compounds which are within the scope of the present invention can be derived by those of ordinary skill in the art, for example, as follows:

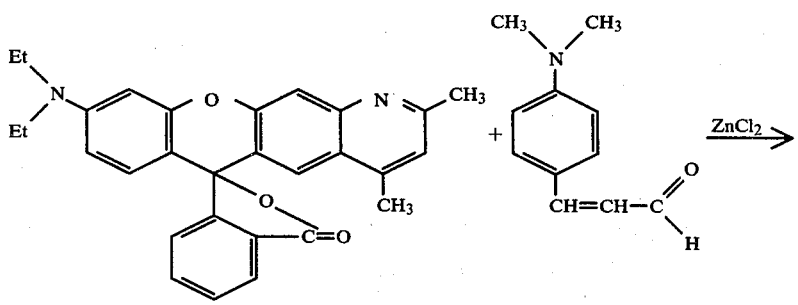

-continued
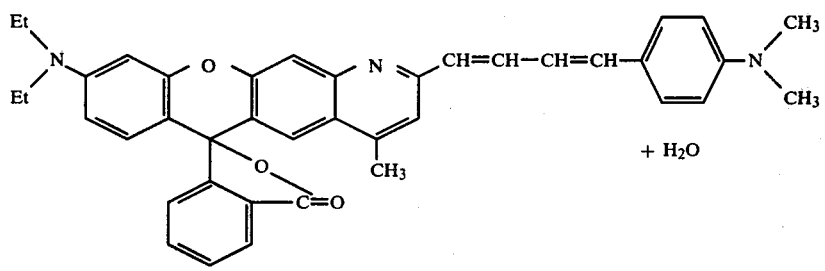
+ H₂O
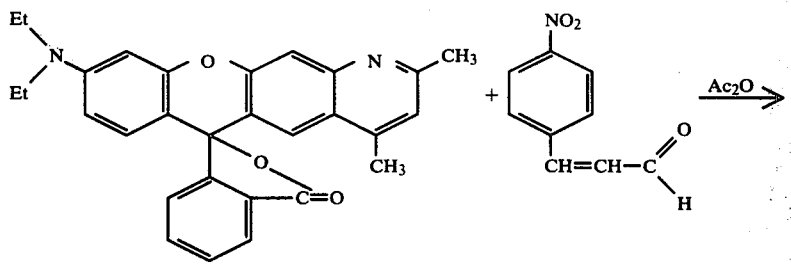
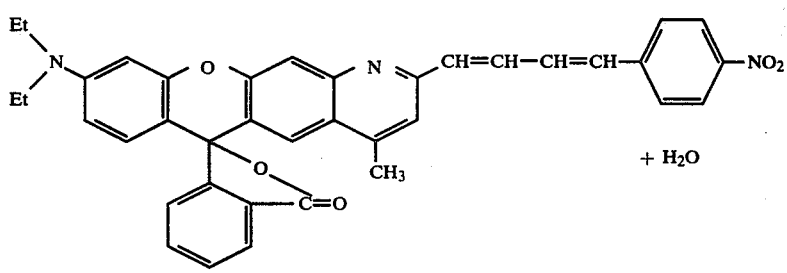
+ H₂O
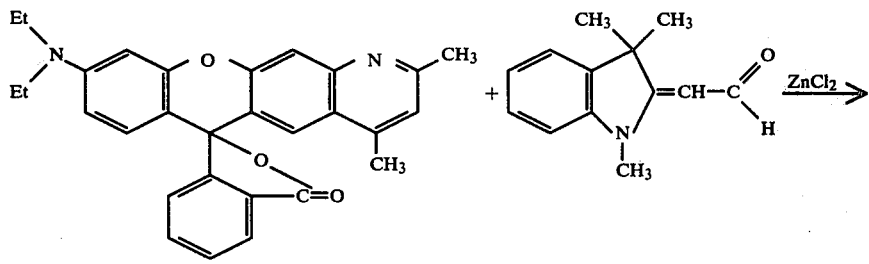
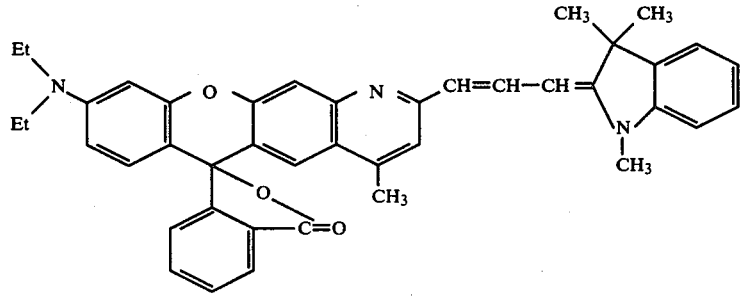
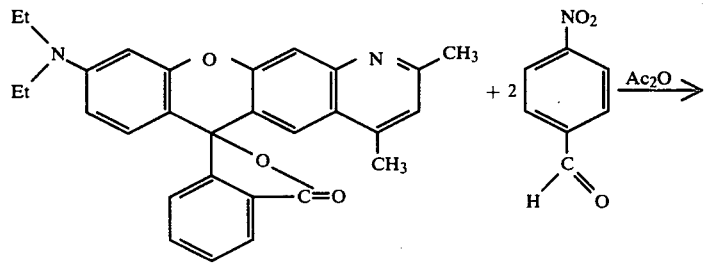

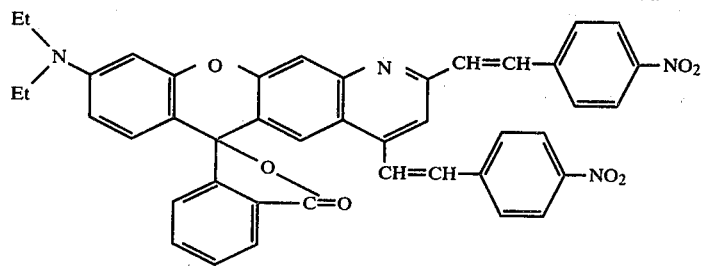

↓ Reduce and methylate

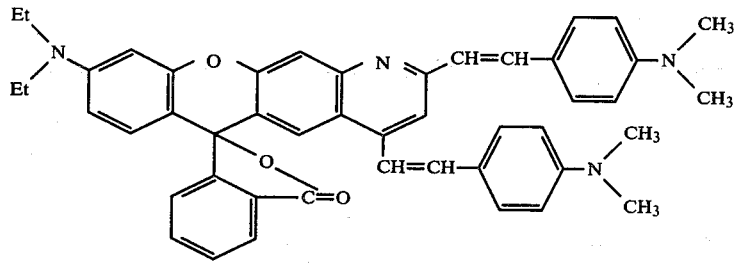

The invention will now be better understood with reference to the following examples.

EXAMPLE 1

Preparation of 7-hydroxy-2,4-dimethyl quinoline.

21.8 grams (0.2 moles) of m-aminophenol were mixed with 22 grams (0.22 moles) of acetylacetone and refluxed for 1½ hours. The reaction was as follows:

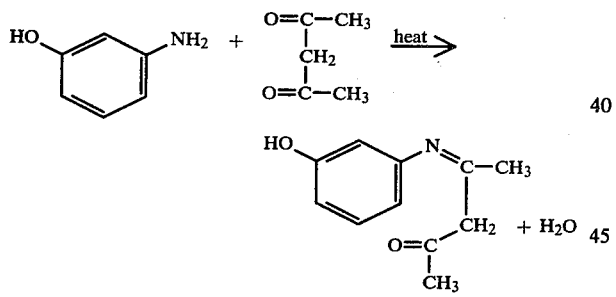

The obtained red solution was cooled and the yellow precipitate which formed was filtered off, washed with water and dried. The solid was then ground in a mortar, reslurried in 200 ml of water, filtered off, washed again with water, dried, and ground in a mortar until a fine powder was obtained. 27 grams of this powder was portionwise added to 90 ml of sulfuric acid with vigorous stirring. The temperature was maintained below 10° C. with an ice-salt bath. When all the solids were in solution, it was heated on a steam bath for 30 minutes and cooled. 7-hydroxy-2,4-dimethyl quinoline was formed according to the reaction:

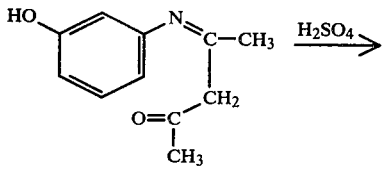

EXAMPLE 2

Preparation of 9-(diethylamino)-2,4-dimethyl spiro [6H-[1] benzopyrano-[3,2-g] quinoline-6,1′(3′H)isobenzofuran]-3′-one.

To the solution obtained in Example 1 was added 85 ml of sulfuric acid and then 43.8 grams (0.14 moles) of 4′-diethylamino 2′-hydroxybenzoyl benzoic acid. While the resulting solution was stirred, it was heated on a steam bath for 4 hours. The solution was then cooled and slowly added to 2 liters of ice. The resulting slurry was made alkaline with a sodium hydroxide solution and then extracted three times with toluene. The toluene layers were combined (2 liters), washed three times with 1 liter of water and dried over sodium sulfate. The resulting orange solution was treated with activated carbon (DARCO) and filtered. The toluene was then distilled off to leave a volume of 75 ml. On cooling, a pink precipitate of 9-(diethylamino)-2,4-dimethyl spiro [6H-[1] benzopyrano-[3,2g] quinoline-6,1′(3′H)-isobenzofuran]-3′-one was formed. It was filtered off, washed with toluene to remove the color and dried. The reaction sequence was as follows:

-continued

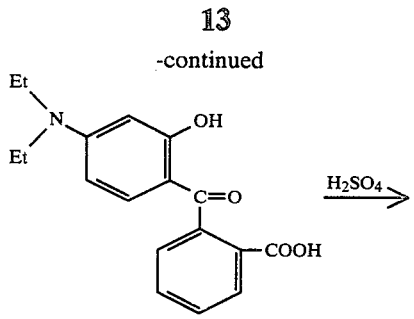

normal HCl was added and the mixture heated on a steam bath for 30 minutes. The excess aldehyde was removed by steam distillation and the mixture filtered. The obtained solids were boiled in a 10% ammonia solution for 30 minutes and the mixture filtered to obtain a dark solid. This solid was then dissolved in 50 ml of boiling toluene, treated with activated charcoal (DARCO) and filtered. Ligroine was added to the toluene solution to precipitate the yellow product. The yield of the filtered product was 0.5 grams. The reaction scheme was as follows

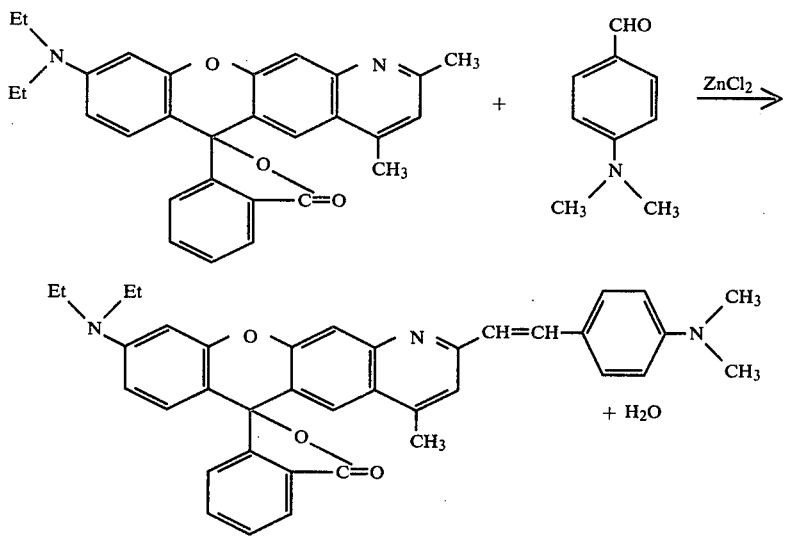

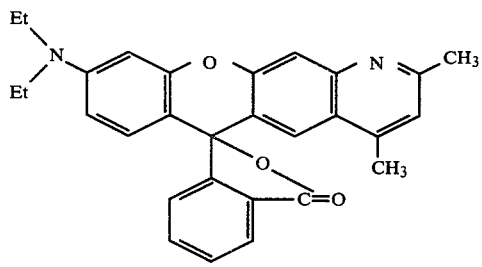

A 10% toluene solution of the fluoran product gave an instantaneous red on an acid-leached clay coating on a paper substrate (CF).

EXAMPLE 3

Preparation of 9-(diethylamino)-2-(4-dimethylaminostyryl)-4-methylspiro [6H-[1] benzopyrano [3,2-g] quinoline-6,1'(3'H)-isobenzofuran]-3'-one.

1.4 grams (0.003 moles) of 9-(diethylamino)-2,4-dimethylspiro [6H-[1] benzopyrano [3,2-g] quinoline-6,1'(3'H)isobenzofuran]-3'-one, 0.5 grams (0.003 moles) of p-dimethylaminobenzaldehyde, and 0.1 grams of zinc chloride were mixed in a test tube and then heated in an oil bath at 180°–185° C. for 2 hours. Then 36 ml of A 10% toluene solution of the fluoran gave an instantaneous light violet on an acid-leached coating on a paper substrate (CF).

EXAMPLE 4

Preparation of 9-(diethylamino)-2-(4-nitrostyryl)-4-methylspiro[6H-[1] benzopyrano [3,2-g] quinoline-6,1'(3'H)-isobenzofuran]-3'-one.

2.3 grams (0.005 moles) of 9-(diethylamino)-2-(4-dimethylaminostyryl)-4-methylspiro [6H-[1] benzopyrano [3,2-g] quinoline-6,1'(3'H)-isobenzofuran]-3'-one, 0.6 grams (0.005 moles) of p-nitrobenzaldehyde and 0.5 grams (0.005 moles) of acetic anhydride were mixed in a flask fitted with a reflux condenser, then heated in an oil bath at 160° C. for 4 hours. The bath was cooled and 50 ml of water was added. The mixture was then made alkaline with ammonia, extracted with 100 ml of toluene, dried over sodium sulfate, treated with activated charcoal (DARCO) and filtered. The volume of the solution was reduced to 25 ml by evaporation of the toluene. Ligroine was added to precipitate the product. The yellow-orange solids were filtered off and dried to yield 1.5 grams of product. The reaction sequence was as follows:

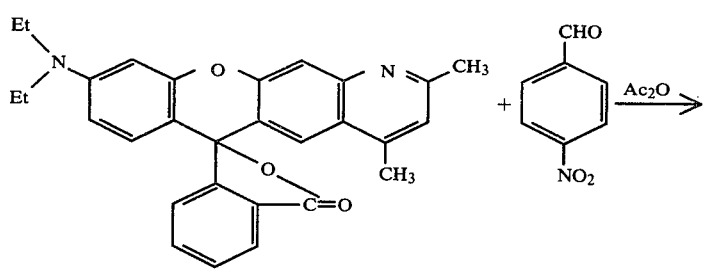

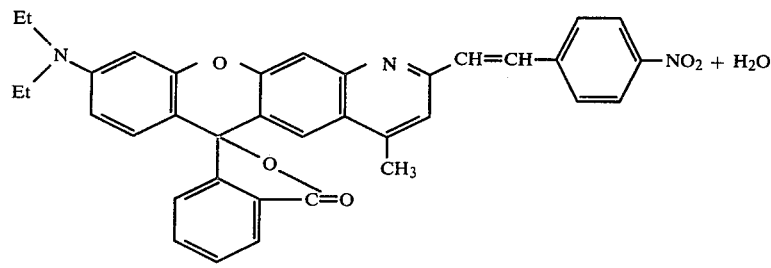

A 10% toluene solution of the product gave an instantaneous red on CF.

EXAMPLE 5

Preparation of 9-(diethylamino)-2-(4-aminostyryl)-4-methylspiro [6H-[1] benzopyrano [3,2 g] quinoline-6,1′(3′H)-isobenzofuran]-3′-one.

The product of Example 4 (0.0025 moles) was refluxed in 50 ml of alcohol. Then 2.3 grams of stannous chloride dissolved in 3 ml of HCl was added dropwise at reflux to produce a vigorous reaction. The mixture turned red, then purple. Reflux was continued for 30 minutes. The mixture was then cooled, poured into 500 ml of water, made alkaline with ammonia and extracted twice with 100 ml of toluene. The toluene layers were combined, dried over sodium sulfate, treated with activated charcoal (DARCO) and filtered. The volume was reduced to 25 ml by evaporation of the toluene. Ligroine was added at the boil until the product stayed in solution. The solution was cooled and the yellow solids were filtered off. The reaction scheme is as follows:

A 10% toluene solution of the fluoran gave an instantaneous dark purple on an acid-leached clay coating on a paper substrate (CF).

EXAMPLE 6

Evaluation of fluoran compound of Example 2 as precursor 1.00 grams of the fluoran compound produced in Example 2 were mixed with 20 grams of R-300 solvent (a commercial product of Kureha Corporation of America which is a mixture of isomeric disopropyl naphthalenes and which is generally disclosed in U.S. Pat. No. 3,806,463 to Konishi et al.) and this admixture was warmed slightly on a hot plate until a clear solution (solution A) was obtained. Thereafter solution A was allowed to cool to room temperature. Then 3.26 grams of terephthaloyl chloride were added to 10.0 grams of R-300 solvent and this mixture was warmed slightly on a hot plate until a clear solution (solution B) was obtained. Solution B was then allowed to cool to room temperature. After solutions A and B were prepared, 100 grams of an aqueous solution containing 2.0 weight

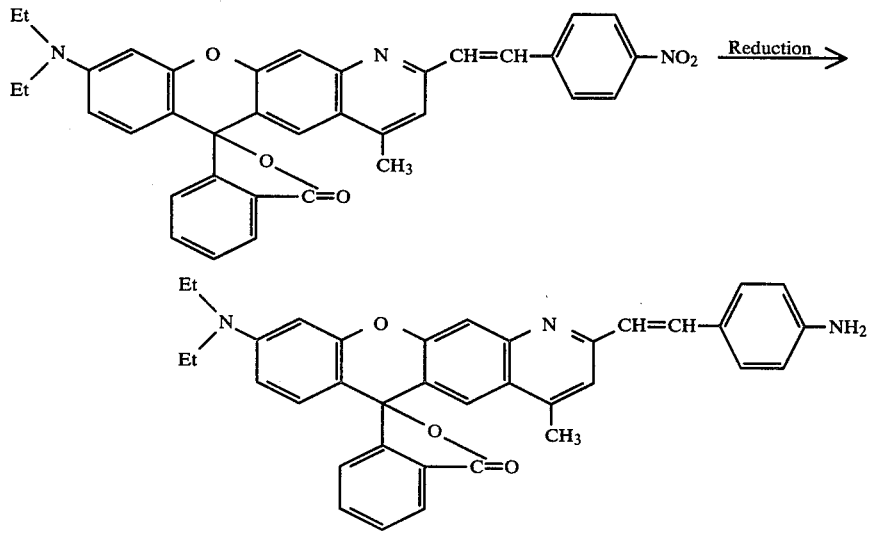

percent Elvanol 50-42 (a commercial product of E. I. duPont de Nemours which is a polyvinyl alcohol with 87% to 89% hydrolysis and a viscosity of 35 to 45 cps in a 4% aqueous solution at 20° C.) were placed in a semi-micro Waring blender and then solutions A and B were mixed together at room temperature and the resultant solution was added to the Elvanol solution in the blender. The blender was activated and high shear agitation was continued for about two minutes until an emulsion having a dispersed phase particle size of about 2 to 10 microns was obtained. In this emulsion, the aqueous solution containing the Elvanol polyvinyl alcohol formed the continuous phase and the solution containing the R-300 solvent, the fluoran compound, and the terephthaloyl chloride formed the dispersed phase. The emulsion was then transferred to a suitable container such as a beaker and was stirred with a variable speed mechanical stirrer at 300 to 500 rpm, while an aqueous solution containing 1.86 grams of diethylenetriamine, 1.2 grams of sodium carbonate and 20 ml of water was added. Stirring was continued for about 24 hours until a stable pH of about 8.0 was observed. At this time the particles of dispersed phase had become individually encapsulated in a polyamide shell. The slurry containing the microcapsules, and having the Elvanol polyvinyl alcohol binder in the continuous phase, was then drawn down on a 13 pound neutral base continuous bond paper sheet at a coating weight of approximately 2.34 to 3.04 gms per square meter and the coated sheet was oven dried at a temperature of 110° C. for about 30 to 45 seconds. The dry coating on the paper sheet was slightly pink. The dry coating of microcapsules containing the fluoran derivative was then brought into contact with an acid-leached bentonite-type clay coating on the surface of another sheet of paper and when an impression was made on the reverse side of the sheet coated with microcapsules, a corresponding reddish pink-colored reproduction of such impression immediately appeared on the acid-leached bentonite-type clay coating.

It should again be noted that the present invention contemplates fluoran compounds wherein the amino nitrogen atom carries either hydrogen atoms, methyl groups, ethyl groups, propyl groups, butyl groups, pentyl groups, or any mixture of two of the foregoing. Also, other solvents for color precursors are known to those skilled in the art to which this invention pertains, and any solvent for the 9-(diethylamino)-2,4-dimethyl-spiro [6H-[1] benzopyrano [3,2q] quinoline-6,1′(3′H)-isobenzofuran]-3′-one compounds which does not substantially interfere with the formation of color when the compound is contacted with a co-reactant may be utilized, such as for example, dibutyl phthalate. Finally, it should be appreciated that the compounds of the present invention are useful generally in the production and generation of colored marks and it is not critical to the present invention that the same be utilized in a copying system or in a microencapsulated form.

EXAMPLE 7

Evaluation of Fluoran Compound of Example 3 as Precursor 0.4 grams of the fluoran compound produced in Example 3 were mixed with 8.0 grams of R-300 solvent, and this mixture was warmed slightly on a hot plate until a clear solution (solution A) was obtained. Thereafter solution A was allowed to cool to room temperature. Then 1.30 grams of terephthaloyl chloride were added to 4.0 grams of R-300 solvent and this mixture was warmed slightly on a hot plate until a clear solution (solution B) was obtained. After solutions A and B were prepared, 40 grams of an aqueous solution containing 2.0 weight percent Elvanol 50-42 were placed in a semi-micro Waring blender and then solutions A and B were mixed together at room temperature and the resultant solution was added to the Elvanol solution in the blender. The blender was activated and high shear agitation was continued for about two minutes until an emulsion having a dispersed phase particle size of about 2 to 10 microns was obtained. In this emulsion, the aqueous solution containing 0.74 grams of diethylenetriamine, 0.48 grams of sodium carbonate and 8 ml of water was added. Stirring was continued for about 24 hours until a stable pH of about 8.0 was observed. At this time, the particles of dispersed phase had become individually encapsulated in a polyamide shell. The slurry containing the microcapsules, and having the Elvanol polyvinyl alcohol binder in the continuous phase, was then drawn down on a 13 pound neutral base continuous bond paper sheet at a coating weight of approximately 2.34 to 3.04 gms per square meter and the coated sheet was oven dried at a temperature of 110° C. for about 30 to 45 seconds. The dry coating on the paper sheet was slightly yellow. The dry coating of microcapsules containing the fluoran derivative was then brought into contact with an acid-leached bentonite-type clay coating on the surface of another sheet of paper and when an impression was made on the reverse side of the sheet coated with microcapsules, a corresponding purple-colored reproduction of such impression immediately appeared on the acid-leached bentonite-type clay coating.

I claim:

1. A chromogenic 9-dialkylamino-spiro [6H-[1] benzopyrano [3,2g] quinoline-6,1′(3′H)-isobenzofuran]-3′-one having the following structural formula:

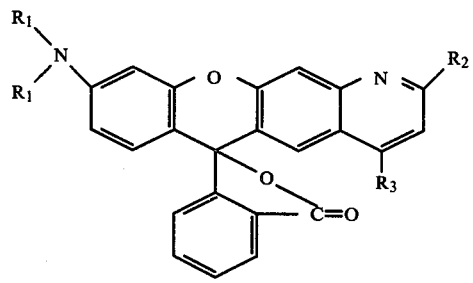

wherein each $R_1$ represents a lower alkyl group having from one to five carbon atoms and wherein each of $R_2$ and $R_3$ represents either a methyl group or a group which includes a methylene bridge resonance path having up to four carbon atoms, but wherein when $R_3$ is a methylene bridge resonance path-containing group, $R_2$ is not a methyl group, said methylene bridge resonance path comprising a substituted alkenyl group 2 to 4 carbon atoms in which the substituents are selected from the group of unsubstituted phenyl, unsubstituted naphthyl, phenyl substituted with a nitro group, phenyl substituted with an amino group, naphthyl substituted with a nitro group, naphthyl substituted with an amino group, and a

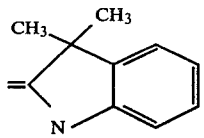

radical.

2. A chromogenic compound as defined in claim 1 wherein $R_1$ is selected from the group consisting of methyl, ethyl, propyl, butyl or pentyl.

3. A chromogenic compound as defined in claim 1 wherein $R_2$ and $R_3$ are both methyl.

4. A chromogenic compound as defined in claim 1 wherein $R_2$ is

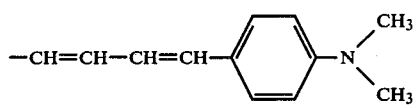

and $R_3$ is methyl.

5. A chromogenic compound as defined in claim 1 wherein $R_2$ is

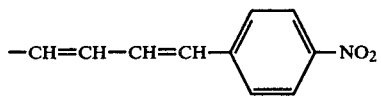

and $R_3$ is methyl.

6. A chromogenic compound as defined in claim 1 wherein $R_2$ is

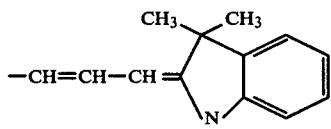

and $R_3$ is methyl.

7. A chromogenic compound as defined in claim 1 wherein $R_2$ is

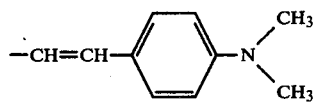

and $R_3$ is

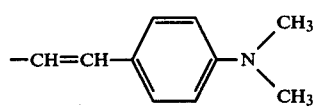

8. A chromogenic compound as defined in claim 1 wherein $R_2$ is

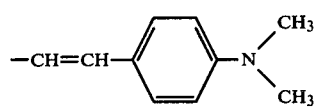

and $R_3$ is methyl.

9. A chromogenic compound as defined in claim 1 wherein $R_2$ is

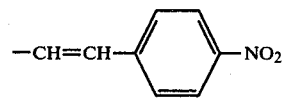

and $R_3$ is methyl.

10. In a pressure-sensitive recording system comprising a layer of microcapsules containing a substantially colorless color precursor compound and a layer of an electron-acceptor material, the improvement which comprises utilizing, as said color precursor compound, a compound as set forth in claim 1.

11. In a pressure-sensitive recording system comprising a layer of microcapsules containing a substantially colorless color precursor compound and a layer of an electron-acceptor material, the improvement which comprises utilizing, as said color precursor compound, a compound as set forth in claim 3.

12. In a pressure-sensitive recording system comprising a layer of microcapsules containing a substantially colorless color precursor compound and a layer of an electron-acceptor material, the improvement which comprises utilizing, as said color precursor compound, a compound as set forth in claim 4.

13. In a pressure-sensitive recording system comprising a layer of microcapsules containing a substantially colorless color precursor compound and a layer of an electron-acceptor material, the improvement which comprises utilizing, as said color precursor compound, a compound as set forth in claim 5.

14. In a pressure-sensitive recording system comprising a layer of microcapsules containing a substantially colorless color precursor compound and a layer of an electron-acceptor material, the improvement which comprises utilizing, as said color precursor compound, a compound as set forth in claim 6.

15. In a pressure-sensitive recording system comprising a layer of microcapsules containing a substantially colorless color precursor compound and a layer of an electron-acceptor material, the improvement which comprises utilizing, as said color precursor compound, a compound as set forth in claim 7.

16. In a pressure-sensitive recording system comprising a layer of microcapsules containing a substantially colorless color precursor compound and a layer of an electron-acceptor material, the improvement which comprises utilizing, as said color precursor compound, a compound as set forth in claim 8.

17. In a pressure-sensitive recording system comprising a layer of microcapsules containing a substantially colorless color precursor compound and a layer of an electron-acceptor material, the improvement which comprises utilizing, as said color precursor compound, a compound as set forth in claim 9.

18. In a pressure-sensitive recording system comprising a layer containing a substantially colorless color-precursor compound and a layer of an electron-acceptor material, the improvement which comprises utilizing, as said color-precursor compound, a compound as set forth in claim 1.

19. In a pressure-sensitive recording system comprising a layer containing a substantially colorless color-precursor compound and a layer of an electron-acceptor material, the improvement which comprises utilizing, as said color-precursor compound, a compound as set forth in claim 3.

20. In a pressure-sensitive recording system comprising a layer containing a substantially colorless color-precursor compound and a layer of an electron-acceptor material, the improvement which comprises utilizing, as said color-precursor compound, a compound as set forth in claim 4.

21. In a pressure-sensitive recording system comprising a layer containing a substantially colorless color-precursor compound and a layer of an electron-acceptor material, the improvement which comprises utilizing, as said color-precursor compound, a compound as set forth in claim 5.

22. In a pressure-sensitive recording system comprising a layer containing a substantially colorless color-precursor compound and a layer of an electron-acceptor material, the improvement which comprises utilizing, as said color-precursor compound, a compound as set forth in claim 6.

23. In a pressure-sensitive recording system comprising a layer containing a substantially colorless color-precursor compound and a layer of an electron-acceptor material, the improvement which comprises utilizing, as said color-precursor compound, a compound as set forth in claim 7.

24. In a pressure-sensitive recording system comprising a layer containing a substantially colorless color-precursor compound and a layer of an electron-acceptor material, the improvement which comprises utilizing, as said color-precursor compound, a compound as set forth in claim 8.

25. In a pressure-sensitive recording system comprising a layer containing a substantially colorless color-precursor compound and a layer of an electron-acceptor material, the improvement which comprises utilizing, as said color-precursor compound, a compound as set forth in claim 9.

* * * * *